United States Patent [19]

Matsukawa et al.

[11] Patent Number: 5,814,505
[45] Date of Patent: Sep. 29, 1998

[54] PROCESS FOR PRODUCING GLYCINE-N-METHYL TRANSFERASE USING RECOMBINANT DNA

[75] Inventors: Hirokazu Matsukawa; Tsuyoshi Fujita, both of Osaka-fu, Japan

[73] Assignee: Oriental Yeast Co., Ltd., Tokyo, Japan

[21] Appl. No.: 489,141

[22] Filed: Jun. 9, 1995

[30] Foreign Application Priority Data

Jul. 22, 1994 [JP] Japan .................................. 6-191197

[51] Int. Cl.$^6$ .............................. C12N 9/10; C12N 1/20; C12N 15/00; C07H 21/04
[52] U.S. Cl. ................. 435/193; 435/252.3; 435/252.33; 435/254.11; 435/320.1; 435/325; 536/23.2
[58] Field of Search ................................. 435/193, 252.3, 435/252.33, 320.1, 254.11, 325; 536/23.2

[56] References Cited

PUBLICATIONS

Biochemical and Biophysical Research Communications, vol. 124, No. 1, 1984, pp. 44–50, H. Ogawa et al.: "Molecular cloning of cDNA for rat glycine methyltransferase".

Heady et al, Purification and Characterization of Glyci$_{ne}$ N–Methyltransferase, Journal of Biol Chem., vol. 248, No. 1, pp. 69–72, Jan. 10, 1973.

Gegner et al, Signal Transduction in Bacteria: CheW Forms a Reversible Complex with the Protein Kinase CheA, Proc. Natl. Acad. Sci., vol. 88, pp. 750–754, Feb. 1991.

Muchmore et al, [3] Experssion and Nitrogen–15 Labeling of Proteins for Proton and Nitrogen–15 Nuclear Magnetic Resonance, Methods in Enzymology, vol. 177, pp. 44–73, 1989.

Lederberg et al, Transformation of Salmonella typhrimurium by Plasmid Deoxyribonucleic Acid, Journal of Bacteriology, vol. 119, No. 3, pp. 1072–1074, Sep. 1974.

Ogawa et al. (1987) Eur. J. Biochem. 168(1): 141–151.

Georgiou (1988) AIChE J. 34(8): 1233–1248.

*Primary Examiner*—Robert A. Wax
*Assistant Examiner*—Lisa J. Hobbs
*Attorney, Agent, or Firm*—Browdy and Neimark

[57] ABSTRACT

GMT is produced by *E. coli* transformant with an expression vector having introduced therein cDNA of glycine-N-methyl transferase (GMT) derived from rat liver. This process can produce GMT of a high purity and a high activity on an industrial scale.

20 Claims, 3 Drawing Sheets

FIG. 1

CAGGATGGTGGACAGCGTGTACCGTACCCGCTCCCTGGGGGTGGCGGCCGAAGGGATCCC
CGACCAGTATGCGGATGGGGAGGCCGCACGTGTGTGGCAGCTGTACATCGGGGACACCCG
CAGCCGTACTGCAGAGTACAAGGCGTGGTTGCTTGGGCTGCTGCGCCAGCACGGGTGCCA
CCGGGTGCTGGACGTGGCCTGTGGCACAGGAGTGGACTCGATTATGCTGGTGGAAGAGGG
CTTTAGCGTCACGAGTGTGGATGCCAGCGACAAGATGCTGAAATACGCACTGAAGGAGCG
CTGGAACCGGAGGAAGGAGCCAGCCTTTGACAAGTGGGTCATTGAAGAAGCCAACTGGTT
GACTCTGGACAAAGATGTGCCAGCAGGAGATGGCTTTGACGCTGTCATCTGCCTTGGGAA
CAGTTTTGCTCACCTGCCGGACAGCAAAGGTGACCAGAGTGAGCACCGGCTGGCGCTAAA
GAACATCGCAAGCATGGTGCGGCCCGGGGGCCTGCTGGTCATCGACCACCGCAACTACGA
CTACATCCTCAGCACGGGCTGTGCACCCCAGGGAAGAACATCTACTATAAGAGTGACCT
GACCAAGGACATTACGACGTCAGTGCTGACAGTAAACAACAAAGCCCACATGGTAACCCT
GGACTACACAGTGCAGGTGCCAGGTGCTGGCAGAGATGGCGCTCCTGGCTTCAGTAAGTT
TCGGCTCTCTTACTACCCACACTGTTTGGCGTCTTTCACGGAGTTGGTCCAAGAAGCCTT
TGGGGGCAGGTGCCAGCACAGCGTCCTGGGTGACTTCAAGCCTTACAGGCCCGGCCAGGC
CTACGTTCCCTGCTACTTCATCCACGTGCTCAAGAAGACAGGCTGAGCCTGGCTCCGGCT
CCCACCCTAAGACCATCGCCTACCACAGATATTGCAGAGATGTGGGGGGCAGGCAAACAG
GGAGTCGACAATACAGCCTTCCCTTGCC

FIG. 2

MVDSVYRTRSLGVAAEGIPDQYADGEAARVWQLYIGDTRSRTAEYKAWLL
GLLRQHGCHRVLDVACGTGVDSIMLVEEGFSVTSVDASDKMLKYALKERW
NRRKEPAFDKWVIEEANWLTLDKDVPAGDGFDAVICLGNSFAHLPDSKGD
QSEHRLALKNIASMVRPGGLLVIDHRNYDYILSTGCAPPGKNIYYKSDLT
KDITTSVLTVNNKAHMVTLDYTVQVPGAGRDGAPGFSKFRLSYYPHCLAS
FTELVQEAFGGRCQHSVLGDFKPYRPGQAYVPCYFIHVLKKTG

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 988 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 5..886

( x i ) SEQUENCE DESCRIPTION: SEQ ID NO:1:

```
CAGG ATG GTG GAC AGC GTG TAC CGT ACC CGC TCC CTG GGG GTG GCG GCC         49
     Met Val Asp Ser Val Tyr Arg Thr Arg Ser Leu Gly Val Ala Ala
     1               5                   10                  15

GAA GGG ATC CCC GAC CAG TAT GCG GAT GGG GAG GCC GCA CGT GTG TGG         97
Glu Gly Ile Pro Asp Gln Tyr Ala Asp Gly Glu Ala Ala Arg Val Trp
                20              25                  30

CAG CTG TAC ATC GGG GAC ACC CGC AGC CGT ACT GCA GAG TAC AAG GCG         145
Gln Leu Tyr Ile Gly Asp Thr Arg Ser Arg Thr Ala Glu Tyr Lys Ala
            35              40                  45

TGG TTG CTT GGG CTG CTG CGC CAG CAC GGG TGC CAC CGG GTG CTG GAC         193
Trp Leu Leu Gly Leu Leu Arg Gln His Gly Cys His Arg Val Leu Asp
        50              55                  60

GTG GCC TGT GGC ACA GGA GTG GAC TCG ATT ATG CTG GTG GAA GAG GGC         241
Val Ala Cys Gly Thr Gly Val Asp Ser Ile Met Leu Val Glu Glu Gly
65              70                  75

TTT AGC GTC ACG AGT GTG GAT GCC AGC GAC AAG ATG CTG AAA TAC GCA         289
Phe Ser Val Thr Ser Val Asp Ala Ser Asp Lys Met Leu Lys Tyr Ala
80              85                  90                  95

CTG AAG GAG CGC TGG AAC CGG AGG AAG GAG CCA GCC TTT GAC AAG TGG         337
Leu Lys Glu Arg Trp Asn Arg Arg Lys Glu Pro Ala Phe Asp Lys Trp
            100                 105                 110

GTC ATT GAA GAA GCC AAC TGG TTG ACT CTG GAC AAA GAT GTG CCA GCA         385
Val Ile Glu Glu Ala Asn Trp Leu Thr Leu Asp Lys Asp Val Pro Ala
        115                 120                 125

GGA GAT GGC TTT GAC GCT GTC ATC TGC CTT GGG AAC AGT TTT GCT CAC         433
Gly Asp Gly Phe Asp Ala Val Ile Cys Leu Gly Asn Ser Phe Ala His
    130                 135                 140

CTG CCG GAC AGC AAA GGT GAC CAG AGT GAG CAC CGG CTG GCG CTA AAG         481
Leu Pro Asp Ser Lys Gly Asp Gln Ser Glu His Arg Leu Ala Leu Lys
145                 150                 155

AAC ATC GCA AGC ATG GTG CGG CCC GGG GGC CTG CTG GTC ATC GAC CAC         529
Asn Ile Ala Ser Met Val Arg Pro Gly Gly Leu Leu Val Ile Asp His
160                 165                 170                 175

CGC AAC TAC GAC TAC ATC CTC AGC ACG GGC TGT GCA CCC CCA GGG AAG         577
Arg Asn Tyr Asp Tyr Ile Leu Ser Thr Gly Cys Ala Pro Pro Gly Lys
            180                 185                 190

AAC ATC TAC TAT AAG AGT GAC CTG ACC AAG GAC ATT ACG ACG TCA GTG         625
Asn Ile Tyr Tyr Lys Ser Asp Leu Thr Lys Asp Ile Thr Thr Ser Val
        195                 200                 205

CTG ACA GTA AAC AAC AAA GCC CAC ATG GTA ACC CTG GAC TAC ACA GTG         673
Leu Thr Val Asn Asn Lys Ala His Met Val Thr Leu Asp Tyr Thr Val
    210                 215                 220
```

```
CAG  GTG  CCA  GGT  GCT  GGC  AGA  GAT  GGC  GCT  CCT  GGC  TTC  AGT  AAG  TTT      721
Gln  Val  Pro  Gly  Ala  Gly  Arg  Asp  Gly  Ala  Pro  Gly  Phe  Ser  Lys  Phe
     225                      230                      235

CGG  CTC  TCT  TAC  TAC  CCA  CAC  TGT  TTG  GCG  TCT  TTC  ACG  GAG  TTG  GTC      769
Arg  Leu  Ser  Tyr  Tyr  Pro  His  Cys  Leu  Ala  Ser  Phe  Thr  Glu  Leu  Val
240                 245                      250                           255

CAA  GAA  GCC  TTT  GGG  GGC  AGG  TGC  CAG  CAC  AGC  GTC  CTG  GGT  GAC  TTC      817
Gln  Glu  Ala  Phe  Gly  Gly  Arg  Cys  Gln  His  Ser  Val  Leu  Gly  Asp  Phe
                    260                      265                      270

AAG  CCT  TAC  AGG  CCC  GGC  CAG  GCC  TAC  GTT  CCC  TGC  TAC  TTC  ATC  CAC      865
Lys  Pro  Tyr  Arg  Pro  Gly  Gln  Ala  Tyr  Val  Pro  Cys  Tyr  Phe  Ile  His
               275                      280                      285

GTG  CTC  AAG  AAG  ACA  GGC  TGA  GCCTGGCTCC  GGCTCCCACC  CTAAGACCAT               916
Val  Leu  Lys  Lys  Thr  Gly  *
          290

CGCCTACCAC  AGATATTGCA  GAGATGTGGG  GGGCAGGCAA  ACAGGGAGTC  GACAATACAG              976

CCTTCCCTTG  CC                                                                      988
```

( 2 ) INFORMATION FOR SEQ ID NO:2:

( i ) SEQUENCE CHARACTERISTICS:
        ( A ) LENGTH: 293 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Val  Asp  Ser  Val  Tyr  Arg  Thr  Arg  Ser  Leu  Gly  Val  Ala  Ala  Glu
1                   5                   10                      15

Gly  Ile  Pro  Asp  Gln  Tyr  Ala  Asp  Gly  Glu  Ala  Ala  Arg  Val  Trp  Gln
               20                  25                           30

Leu  Tyr  Ile  Gly  Asp  Thr  Arg  Ser  Arg  Thr  Ala  Glu  Tyr  Lys  Ala  Trp
          35                       40                      45

Leu  Leu  Gly  Leu  Leu  Arg  Gln  His  Gly  Cys  His  Arg  Val  Leu  Asp  Val
     50                       55                      60

Ala  Cys  Gly  Thr  Gly  Val  Asp  Ser  Ile  Met  Leu  Val  Glu  Glu  Gly  Phe
65                       70                       75                           80

Ser  Val  Thr  Ser  Val  Asp  Ala  Ser  Asp  Lys  Met  Leu  Lys  Tyr  Ala  Leu
               85                       90                           95

Lys  Glu  Arg  Trp  Asn  Arg  Arg  Lys  Glu  Pro  Ala  Phe  Asp  Lys  Trp  Val
               100                      105                      110

Ile  Glu  Glu  Ala  Asn  Trp  Leu  Thr  Leu  Asp  Lys  Asp  Val  Pro  Ala  Gly
          115                      120                      125

Asp  Gly  Phe  Asp  Ala  Val  Ile  Cys  Leu  Gly  Asn  Ser  Phe  Ala  His  Leu
     130                      135                      140

Pro  Asp  Ser  Lys  Gly  Asp  Gln  Ser  Glu  His  Arg  Leu  Ala  Leu  Lys  Asn
145                      150                      155                      160

Ile  Ala  Ser  Met  Val  Arg  Pro  Gly  Gly  Leu  Leu  Val  Ile  Asp  His  Arg
               165                      170                      175

Asn  Tyr  Asp  Tyr  Ile  Leu  Ser  Thr  Gly  Cys  Ala  Pro  Pro  Gly  Lys  Asn
               180                      185                      190

Ile  Tyr  Tyr  Lys  Ser  Asp  Leu  Thr  Lys  Asp  Ile  Thr  Thr  Ser  Val  Leu
          195                      200                      205

Thr  Val  Asn  Asn  Lys  Ala  His  Met  Val  Thr  Leu  Asp  Tyr  Thr  Val  Gln
     210                      215                      220

Val  Pro  Gly  Ala  Gly  Arg  Asp  Gly  Ala  Pro  Gly  Phe  Ser  Lys  Phe  Arg
225                      230                      235                      240
```

| Leu | Ser | Tyr | Tyr | Pro | His | Cys | Leu | Ala | Ser | Phe | Thr | Glu | Leu | Val | Gln |
|---|---|---|---|---|---|---|---|---|---|---|---|---|---|---|---|
|   |   |   |   | 245 |   |   |   |   | 250 |   |   |   |   | 255 |   |

| Glu | Ala | Phe | Gly | Gly | Arg | Cys | Gln | His | Ser | Val | Leu | Gly | Asp | Phe | Lys |
|---|---|---|---|---|---|---|---|---|---|---|---|---|---|---|---|
|   |   |   |   | 260 |   |   |   |   | 265 |   |   |   |   | 270 |   |

| Pro | Tyr | Arg | Pro | Gly | Gln | Ala | Tyr | Val | Pro | Cys | Tyr | Phe | Ile | His | Val |
|---|---|---|---|---|---|---|---|---|---|---|---|---|---|---|---|
|   |   | 275 |   |   |   |   | 280 |   |   |   |   | 285 |   |   |   |

| Leu | Lys | Lys | Thr | Gly |
|---|---|---|---|---|
|   |   |   |   | 290 |

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

TGGTTGATAG TGTTTACCGK ACCCGC                                       26

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:4:

CGATAAGCTT AGGGTGGGAG CCG                                         23

(2) INFORMATION FOR SEQ ID NO:5:

(i) SEQUENCE CHARACTERISTICS:
        (A) LENGTH: 882 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:5:

| ATGGTTGATA | GTGTTTACCG | KACCCGCTCC | CTGGGGGTGG | CGGCCGAAGG | GATCCCCGAC | 60 |
|---|---|---|---|---|---|---|
| CAGTATGCGG | ATGGGGAGGC | CGCACGTGTG | TGGCAGCTGT | ACATCGGGGA | CACCCGCAGC | 120 |
| CGTACTGCAG | AGTACAAGGC | GTGGTTGCTT | GGGCTGCTGC | GCCAGCACGG | GTGCCACCGG | 180 |
| GTGCTGGACG | TGGCCTGTGG | CACAGGAGTG | GACTCGATTA | TGCTGGTGGA | AGAGGGCTTT | 240 |
| AGCGTCACGA | GTGTGGATGC | CAGCGACAAG | ATGCTGAAAT | ACGCACTGAA | GGAGCGCTGG | 300 |
| AACCGGAGGA | AGGAGCCAGC | CTTTGACAAG | TGGGTCATTG | AAGAAGCCAA | CTGGTTGACT | 360 |
| CTGGACAAAG | ATGTGCCAGC | AGGAGATGGC | TTTGACGCTG | TCATCTGCCT | TGGGAACAGT | 420 |
| TTTGCTCACC | TGCCGGACAG | CAAAGGTGAC | CAGAGTGAGC | ACCGGCTGGC | GCTAAAGAAC | 480 |
| ATCGCAAGCA | TGGTGCGGCC | CGGGGGCCTG | CTGGTCATCG | ACCACCGCAA | CTACGACTAC | 540 |
| ATCCTCAGCA | CGGGCTGTGC | ACCCCCAGGG | AAGAACATCT | ACTATAAGAG | TGACCTGACC | 600 |
| AAGGACATTA | CGACGTCAGT | GCTGACAGTA | AACAACAAAG | CCCACATGGT | AACCCTGGAC | 660 |
| TACACAGTGC | AGGTGCCAGG | TGCTGGCAGA | GATGGCGCTC | CTGGCTTCAG | TAAGTTTCGG | 720 |

-continued

| | | | | | | |
|---|---|---|---|---|---|---|
| CTCTCTTACT | ACCCACACTG | TTTGGCGTCT | TTCACGGAGT | TGGTCCAAGA | AGCCTTTGGG | 780 |
| GGCAGGTGCC | AGCACAGCGT | CCTGGGTGAC | TTCAAGCCTT | ACAGGCCCGG | CCAGGCCTAC | 840 |
| GTTCCCTGCT | ACTTCATCCA | CGTGCTCAAG | AAGACAGGCT | GA | | 882 |

PROCESS FOR PRODUCING GLYCINE-N-METHYL TRANSFERASE USING RECOMBINANT DNA

DETAILED DESCRIPTION OF THE INVENTION

1. Field of the Invention

The present invention relates to a recombinant vector containing DNA that has the gene information of glycine-N-methyl transferase derived from rat liver, a transformant obtained by using the recombinant vector, and a process for producing the glycine-N-methyl transferase by expressing the gene information of the DNA by means of the transformant.

2. Prior Art

It is known that glycine-N-methyl transferase (hereinafter also referred to as "GMT") catalyzes the following chemical reaction and is present mainly in the liver, kidney and spleen of animals.

glycine+S-adenosylmethionine
→sarcosine+S-adenosylhomocysteine

This enzyme is purified from rabbit liver (J. Biol. Chem., 1973, 248:69–72). It is also reported that this enzyme is obtained from rat liver.

Further, glycine-N-methyl transferase can be used for the determination of glycine by utilizing the above chemical catalytic reaction. Still further, it is extremely useful, in combination with a reaction system that forms glycine, as a reagent for determination of various enzymatic activities or as a reagent for clinical diagnosis.

PROBLEMS TO BE SOLVED BY THE INVENTION

Glycine-N-methyl transferase on which has been reported so far is purified from the internal organs of animals. However, the content of the enzyme in each internal organ is low, and thus it is difficult to obtain this enzyme in large amounts, with the result that the production of the enzyme is costly.

When the above-mentioned enzyme is used for the determination of glycine or for the determination of various enzymatic activities in combination with the chemical reaction system that catalyzes the formation of glycine, a high reactivity of the enzyme with glycine is required. In this regard, it is reported that the Km value of glycine-N-methyl transferase derived from rat liver is 1/10 that of glycine-N-methyl transferase derived from rabbit liver. Since the glycine-N-methyl transferase activity of rat liver is lower than that of rabbit liver, it is quite difficult to provide an industrially available amount of the enzyme.

MEANS TO SOLVE THE PROBLEMS

The present invention has been made to develop a process for industrially and efficiently producing high-purity GMT at a low cost.

In order to achieve the above-mentioned objective, the present inventors have conducted various investigations, and have consequently judged that the extraction of GMT from internal organs of animals is limited. Then they focused on recombinant DNA technology, and have developed a way of mass-producing GMT through recombinant DNA technology.

In order to achieve this, the present inventors first tried to clone cDNA of GMT derived from rat liver, then formed a recombinant vector having an excellent expression property, and inserted the expression vector having the cDNA into *Escherichia coli*. They confirmed that the transformant expresses GMT in a large amount (approximately 10% of the total cell protein). This contributes to the mass production of GMT.

The present invention will be described in more detail below.

Figure 1:
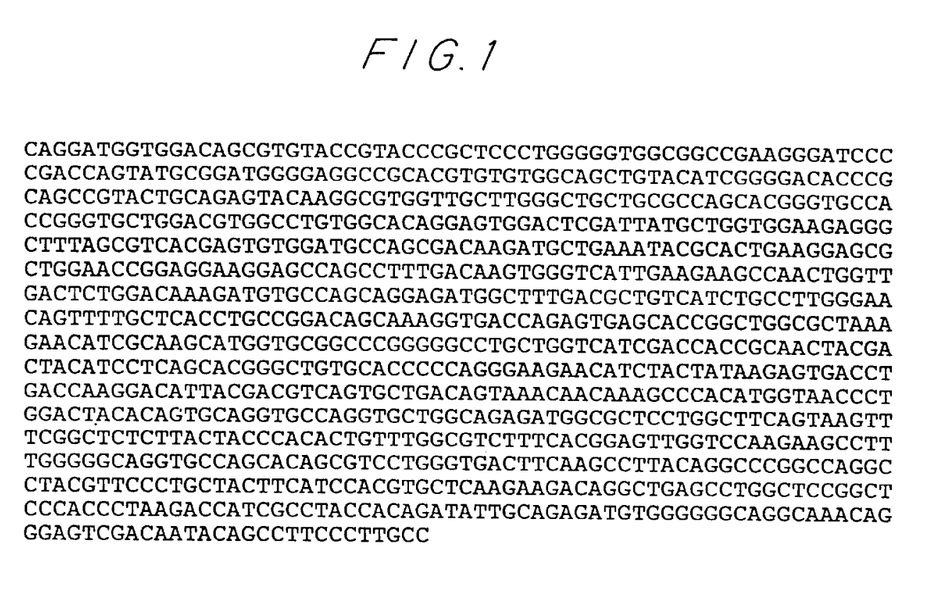
FIG. 1 shows a base sequence of cDNA (SEQ ID NO:1) of GMT derived from rat liver (GMT of rat liver is referred to as "rat liver GMT" or "rGMT" hereinafter.).
Figure 2:
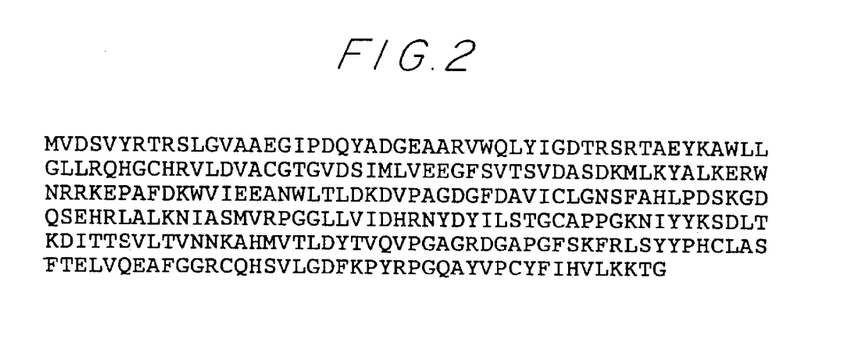
FIG. 2 shows an amino-acid sequence (SEQ ID NO:2) of GMT derived from rat liver.

(1) Formation of an Expression Vector i) Cloning of cDNA of Rat Liver GMT:

Using an antibody from rabbit antiserum against rGMT obtained by immunizing a rabbit with GMT derived from rat liver, rat liver cDNA library (λgt 11) supplied by Clontech Co. was screened in a usual manner to obtain the cDNA of rGMT. The cDNA of the positive clone was transplanted into the plasmid, and the base sequence was determined by the Sanger method as shown in FIG. 1. The deduced amino-acid sequence is shown in FIG. 2. The base sequence of rat liver GMT cDNA from the translation initiation codon to the termination codon is represented by nucleotides 5–886 of SEQ ID NO:1 as shown in the following Sequence on Tables 1, 2 and 3.

TABLE 1

Sequence Listing:
Sequence No. 1
Length of sequence: 988
Type of sequence: nucleic acid
Type of strand: double strand
Topology: linear
Type of sequence: DNA complementary to mRNA (cDNA)
Origin: rat internal organ (liver)
Characteristics of sequence:
symbol showing characteristics: structural gene
location: 5 . . . 886
method of determining characteristics: S
Sequence: Tables 2 to 3

TABLE 2

| | | 13 | | 22 | | 31 | | 40 | | 49 | | 58 |
|---|---|---|---|---|---|---|---|---|---|---|---|---|
| 5' ATG | GTG | GAC | AGC | GTG | TAC | CGT | ACC | CGC | TCC | CTG | GGG | GTG | GCG | GCC | GAA | GGG | ATC |
| Met | Val | Asp | Ser | Val | Tyr | Arg | Thr | Arg | Ser | Leu | Gly | Val | Ala | Ala | Glu | Gly | Ile |

TABLE 2-continued

| | | 67 | | | 76 | | | 85 | | | 94 | | | 103 | | | 112 |
|---|---|---|---|---|---|---|---|---|---|---|---|---|---|---|---|---|---|
| CCC | GAC | CAG | TAT | GCG | GAT | GGG | GAG | GCC | GCA | CGT | GTG | TGG | CAG | CTG | TAC | ATC | GGG |
| Pro | Asp | Gln | Tyr | Ala | Asp | Gly | Glu | Ala | Ala | Arg | Val | Trp | Gln | Leu | Tyr | Ile | Gly |
| | | 121 | | | 130 | | | 139 | | | 148 | | | 157 | | | 166 |
| GAC | ACC | CGC | AGC | CGT | ACT | GCA | GAG | TAC | AAG | GCG | TGG | TTG | CTT | GGG | CTG | CTG | CGC |
| Asp | Thr | Arg | Ser | Arg | Thr | Ala | Glu | Tyr | Lys | Ala | Trp | Leu | Leu | Gly | Leu | Leu | Arg |
| | | 175 | | | 184 | | | 193 | | | 202 | | | 211 | | | 220 |
| CAG | CAC | GGG | TGC | CAC | CGG | GTG | CTG | GAC | GTG | GCC | TGT | GGC | ACA | GGA | GTG | GAC | TCG |
| Gln | His | Gly | Cys | His | Arg | Val | Leu | Asp | Val | Ala | Cys | Gly | Thr | Gly | Val | Asp | Ser |
| | | 229 | | | 238 | | | 247 | | | 256 | | | 265 | | | 274 |
| ATT | ATG | CTG | GTG | GAA | GAG | GGC | TTT | AGC | GTC | ACG | AGT | GTG | GAT | GCC | AGC | GAC | AAG |
| Ile | Met | Leu | Val | Glu | Glu | Gly | Phe | Ser | Val | Thr | Ser | Val | Asp | Ala | Ser | Asp | Lys |
| | | 283 | | | 292 | | | 301 | | | 310 | | | 319 | | | 328 |
| ATG | CTG | AAA | TAC | GGA | CTG | AAG | GAG | CGC | TGG | AAC | CGG | AGG | AAG | GAG | CCA | GCC | TTT |
| Met | Leu | Lys | Tyr | Ala | Leu | Lys | Glu | Arg | Trp | Asn | Arg | Arg | Lys | Glu | Pro | Ala | Phe |
| | | 337 | | | 346 | | | 355 | | | 364 | | | 373 | | | 382 |
| GAC | AAG | TGG | GTC | ATT | GAA | GAA | GCC | AAC | TGG | TTG | ACT | CTG | GAC | AAA | GAT | GTG | CCA |
| Asp | Lys | Trp | Val | Ile | Glu | Glu | Ala | Asn | Trp | Leu | Thr | Leu | Asp | Lys | Asp | Val | Pro |
| | | 391 | | | 400 | | | 409 | | | 418 | | | 427 | | | 436 |
| GCA | GGA | GAT | GGC | TTT | GAC | GCT | GTC | ATC | TGC | CTT | GGG | AAC | AGT | TTT | GCT | CAC | CTG |
| Ala | Gly | Asp | Gly | Phe | Asp | Ala | Val | Ile | Cys | Leu | Gly | Asn | Ser | Phe | Ala | His | Leu |
| | | 445 | | | 454 | | | 463 | | | 472 | | | 481 | | | 490 |
| CCG | GAC | AGC | AAA | GGT | GAC | CAG | AGT | GAG | CAC | CGG | CTG | GCG | CTA | AAG | AAC | ATC | GCA |
| Pro | Asp | Ser | Lys | Gly | Asp | Gln | Ser | Glu | His | Arg | Leu | Ala | Leu | Lys | Asn | Ile | Ala |
| | | 499 | | | 508 | | | 517 | | | 526 | | | 535 | | | 544 |
| AGC | ATG | GTG | CGG | CCC | GGG | GGC | CTG | CTG | GTC | ATC | GAC | CAC | CGC | AAC | TAC | GAC | TAC |
| Ser | Met | Val | Arg | Pro | Gly | Gly | Leu | Leu | Val | Ile | Asp | His | Arg | Asn | Tyr | Asp | Tyr |

TABLE 3

Figure 3:
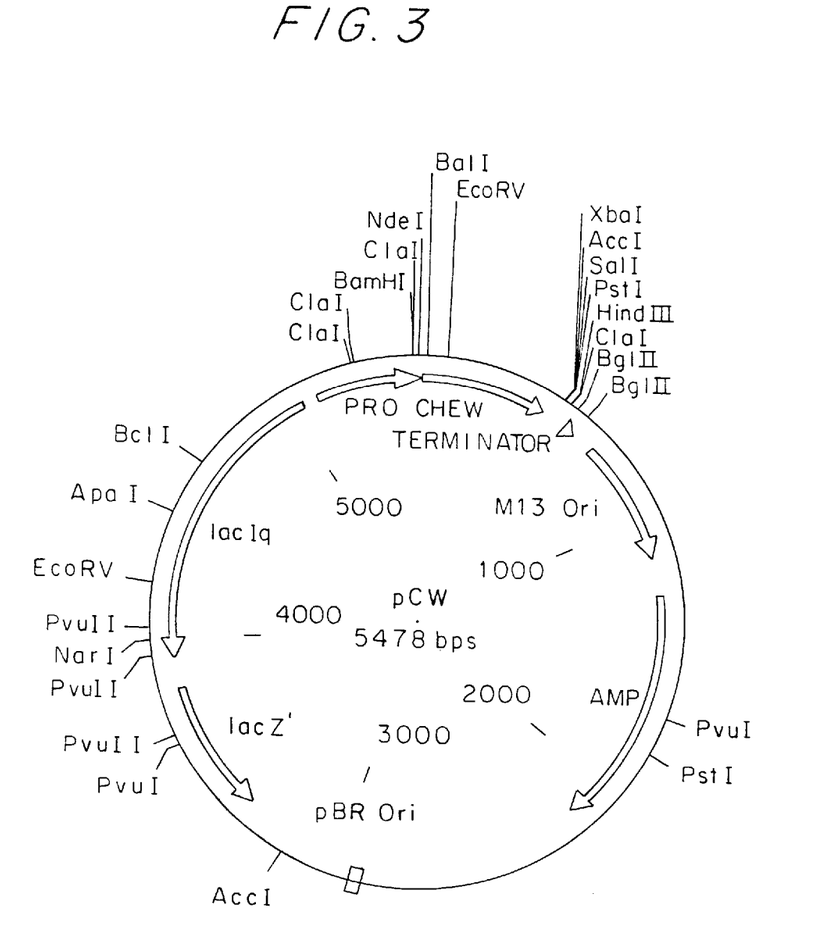
FIG. 3 shows a restriction endonuclease cleavage map of plasmid pCW.

| | | 553 | | | 562 | | | 571 | | | 580 | | | 589 | | | 598 |
|---|---|---|---|---|---|---|---|---|---|---|---|---|---|---|---|---|---|
| ATC | CTC | AGC | ACG | GGC | TGT | GCA | CCC | CCA | GGG | AAG | AAC | ATC | TAC | TAT | AAG | AGT | GAC |
| Ile | Leu | Ser | Thr | Gly | Cys | Ala | Pro | Pro | Gly | Lys | Asn | Ile | Tyr | Tyr | Lys | Ser | Asp |
| | | 607 | | | 616 | | | 625 | | | 634 | | | 643 | | | 652 |
| CTG | ACC | AAG | GAC | ATT | ACG | ACG | TCA | GTG | CTG | ACA | GTA | AAC | AAC | AAA | GCC | CAC | ATG |
| Leu | Thr | Lys | Asp | Ile | Thr | Thr | Ser | Val | Leu | Thr | Val | Asn | Asn | Lys | Ala | His | Met |
| | | 661 | | | 670 | | | 679 | | | 688 | | | 697 | | | 706 |
| GTA | ACC | CTG | GAC | TAC | ACA | GTG | CAG | GTG | CCA | GGT | GCT | GGC | AGA | GAT | GGC | GCT | CCT |
| Val | Thr | Leu | Asp | Tyr | Thr | Val | Gln | Val | Pro | Gly | Ala | Gly | Arg | Asp | Gly | Ala | Pro |
| | | 715 | | | 724 | | | 733 | | | 742 | | | 751 | | | 760 |
| GGC | TTC | AGT | AAG | TTT | CGG | CTC | TCT | TAC | TAC | CCA | CAC | TGT | TTG | GGG | TCT | TTC | ACG |
| Gly | PHe | Ser | Lys | Phe | Arg | Leu | Ser | Tyr | Tyr | Pro | His | Cys | Leu | Ala | Ser | Phe | Thr |
| | | 769 | | | 778 | | | 787 | | | 796 | | | 805 | | | 814 |
| GAG | TTG | GTC | CAA | GAA | GCC | TTT | GGG | GGC | AGG | TGC | CAG | CAC | AGC | GTC | CTG | GGT | GAC |
| Glu | Leu | Val | Gln | Glu | Ala | Phe | Gly | Gly | Arg | Cys | Gln | His | Ser | Val | Leu | Gly | Asp |
| | | 823 | | | 832 | | | 841 | | | 850 | | | 859 | | | 868 |
| TTC | AAG | CCT | TAC | AGG | CCC | GGC | CAG | GCC | TAC | GTT | CCC | TGC | TAC | TTC | ATC | CAC | GTG |
| Phe | Lys | Pro | Tyr | Arg | Pro | Gly | Gln | Ala | Tyr | Val | Pro | Cys | Tyr | Phe | Ile | His | Val |
| | | 877 | | | 886 | | | | | | | | | | | | |
| CTC | AAG | AAG | ACA | GGC | TGA3' | | | | | | | | | | | | |
| Lue | Lys | Lys | Thr | Gly | *** | | | | | | | | | | | | | ii) Formation of an Expression Vector:

Plasmid pCW was employed as a cloning vector. Expression vector pCW-GMT was prepared as follows by inserting rGMT cDNA into plasmid pCW prepared by a method described in, for example, Muchmore et al., Methods in Enzymol., 177, 44–73 (1989) and Gegner and Dahlquist, Proc. Natl. Acad. Sci., USA, 88, 750–754 (1991); the restriction endonuclease cleavage map of plasmid pCW is shown in FIG. 3.

Namely, the multicloning site of plasmid pCW was digested with NdeI, filled in with Klenow, and then digested with Hind III. Subsequently, a sequence (5'TGGT<u>T</u>GA TAG<u>T</u>GT<u>T</u>TACCG (T/G) ACCCGC) (SEQ ID NO:3) from part of the translation initiation codon ATG of the rGMT cDNA was synthesized. In order to increase the translation efficiency, parts of the natural residue were replaced with T (underlined; no change in the amino-acid sequence).

Further, a sequence (5'CGAT AAGCTTAGGGTGGGAGCCG) (SEQ ID NO:4) was synthesized so that Hind III sequence (<u>AAGCTT</u>) was incorporated into a part of the downstream sequence of the termination codon. PCR (polymerase chain reaction) was conducted using these sequences as a primer and the cDNA as a template.

Figure 4:
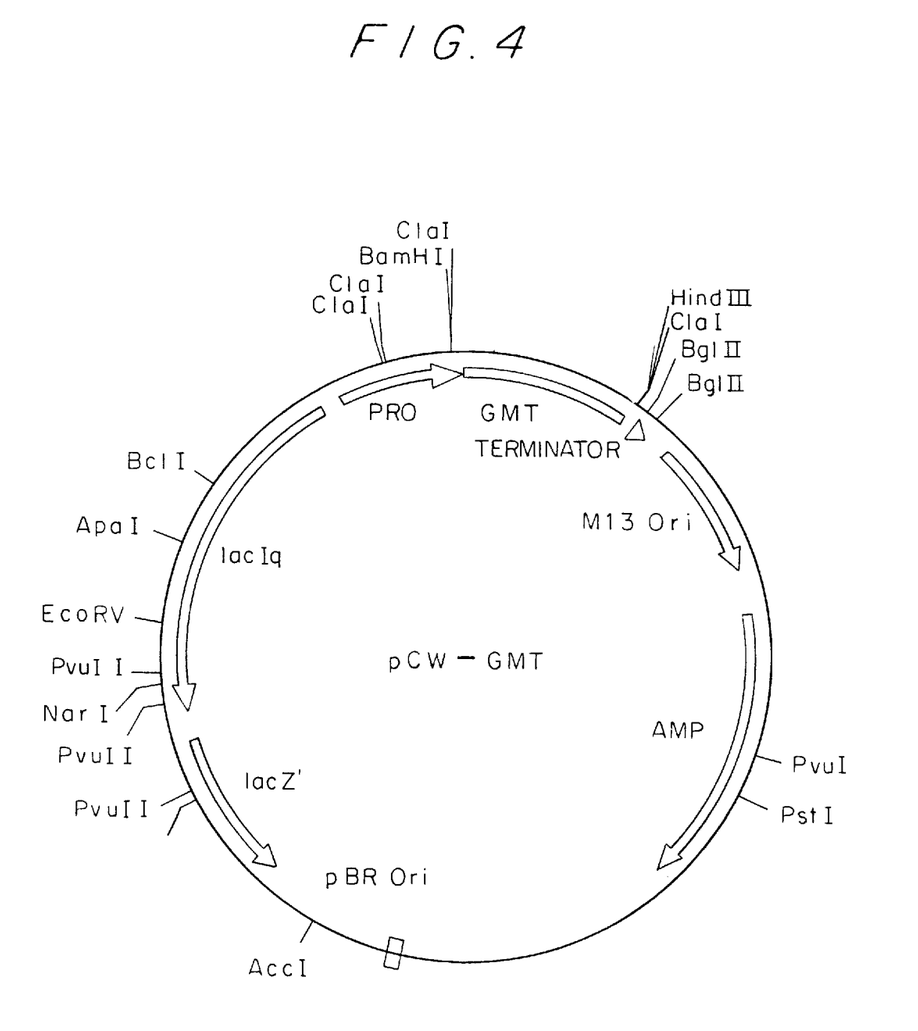
FIG. 4 shows recombinant plasmid pCW-GMT.

The obtained fragment was treated with Hind III, and the treated fragment was inserted into plasmid vector pCW to form recombinant vector pCW-GMT which was the expression vector. FIG. 4 shows recombinant plasmid pCW-GMT.

(2) Formation and Deposition of a Transformant

The recombinant DNA is introduced into a host microorganism in a usual manner. When *Escherichia coli* is used as the host microorganism, for example, a rubidium chloride method is generally used. A calcium method [Lederberg and Cohen, J. Bacteriol., 119, 1072 (1974)] is also available. *Escherichia coli* JM109 belonging to *Escherichia coli* K-12 was used as a host and transformed by introducing the expression vector pCW-GMT thereinto.

The host microorganism (*E. coli* JM 109), in which the recombinant plasmid pCW-GMT has been introduced, exhibited quite a high GMT activity. The thus-obtained transformant was named *E. coli* JM109/pCW-GMT, and was deposited under FERM BP-5078 at the National Institute of Bioscience and Human Technology of the Agency of Industrial Science and Technology 1–3, Higashi 1 chome, Tsukuba-shi, Ibaraki-ken 305, Japan, under the terms of the Budapest Treaty on Apr. 17, 1995; this international deposit is a deposit transferred from national deposit No. FERM P-14435, which was deposited in the same depository on Jul. 18, 1994.

(3) Incubation of a Transformant

*E. coli* JM109/pCW-GMT (FERM BP-5078) was incubated in 2YT culture medium comprising 16 g of polypeptone, 10 g of yeast extract, 5 g of NaCl, 50 mg of ampicillin and 238 mg of isopropyl β-D-thiogalactopyranoside (IPTG) per liter under the following incubation conditions.

Incubation conditions:
  i) The incubation was conducted in a 2-liter Sakaguchi flask filled with 500 ml of the culture medium. Since ampicillin is decomposed through treatment in an autoclave, it was added just before the incubation. IPTG was added at the proliferation stage of *E. coli*.
  ii) Incubation temperature: 35–39° C., preferably 37° C.
  iii) Stirring rate: 80–120 strokes/min, preferably 95 strokes/min by a reciprocating shaker (high aeration is preferable; good results were obtained at 95 strokes/min or more.)
  iv) Incubation time: 10–24 hours, preferably 15–18 hours First, the strain was incubated in 2YT culture medium overnight at 37° C. The culture solution in an amount of 1/100 was then poured into each of two 500 ml Sakaguchi flasks to start the incubation. At the time $A_{600}$ (absorbance at 600 nm) value reached 0.2 or more, IPTG was added such that the final concentration became 1 mM, and the incubation was conducted overnight at 37° C. while shaking.

(4) Recovery and Purification of GMT

After the completion of the incubation, the culture solution was centrifuged at 9,000 rpm for 7 minutes to harvest the cells. The cells were suspended in 50 ml of a solution containing 50 mM tris-HCl (pH 7.5), 2 mM EDTA and 10 mM mercaptoethanol. Subsequently, 1 mg/ml of lysozyme was added to the suspension, and the mixture was retained on ice for 30 minutes while stirring at times. Then, the mixture was frozen at –80° C. for 30 minutes. It is possible that the mixture is stored at –80° C. for a long period of time and is subjected to the following treatment, if required.

The frozen cells were thawed with running water, then sonicated for disruption, and centrifuged at 10,000 rpm for 30 minutes.

The thus-obtained supernatant was passed through a DEAE-cellulose column (DE 52, made by Watman Co., diameter 22 mm, height 10 cm, bed volume 35 ml). A solution containing 10 mM tris-HCl (pH 7.5), 1 mM EDTA, 10 mM mercaptoethanol and 50 mM NaCl was used as a buffer for equilibration and flowing-out, and flowed until $A_{280}$ value reached approximately 0.5. Under these conditions, GMT was not adsorbed into the resin.

Ammonium sulfate was added in an amount of 21 g per 100 ml of the above-mentioned flowing solution (approximately 150 ml). The mixture was retained on ice for 30 minutes or more, and then centrifuged at 10,000 rpm for 30 minutes. Ammonium sulfate (10 g/100 ml) was added to the obtained supernatant. The mixture was retained on ice for 30 minutes or more, and centrifuged at 10,000 rpm for 30 minutes.

The resulting precipitate was dissolved in 2 ml of buffer A containing 10 mM potassium phosphate (pH 7.2), 10 mM EDTA, 10 mM mercaptoethanol and 50 mM NaCl, and passed through Cephacryl S-300 (diameter 32 mm×980 mm; equilibrated with buffer A).

An active fraction was concentrated to 30 g/100 ml with ammonium sulfate. After the completion of the centrifugation, the precipitate was dissolved in a small amount of buffer A, and dialyzed overnight at 4° C. against a solution containing 10 mM potassium phosphate (pH 7.2), 1 mM EDTA and 10 mM mercaptoethanol using a whisking tube as a dialysis membrane. Thereafter, the dialyzate was passed through a DEAE-cellulose column equilibrated with the above-mentioned buffer. The active fraction was concentrated through a collodion bag (ultrafiltration) or with ammonium sulfate to obtain GMT in an amount of from 40 to 80 mg/liter of the culture solution; this product was a single band in SDS-polyacrylamide electrophoresis. The subunit molecular weight of this GMT was approximately 32,600 which was almost the same as that of GMT derived from rat liver. However, N-terminal Val was not blocked. The GMT obtained by using recombinant DNA was stabilized with the addition of dithiothreitol (DTT).

(5) Determination of Activity

The activity of was determined by measuring the decrease of $A_{265}$ value using a spectrophotometer according to the principle of determining the activity as shown in Table 4. The reaction solution contained, per 2 ml, 0.1 mM AdoMet, 10 mM Gly, 50 mM potassium phosphate (pH 7.4), ADA (adenosine deaminase, obtained from Sigma Co.) and AdoHCy (S-adenosylhomocysteine) hydrolase (purified by the present inventors). The determination was conducted in the temperature range of from 25 to 35° C.

TABLE 4

Principle of determining an activity:

EFFECTS OF THE INVENTION

The present invention has succeeded in actually expressing GMT by using the gene of GMT derived from rat liver, and has enabled the mass production of GMT for the first time. Consequently, the present invention is the first to have enabled the mass-production of GMT by incubating the novel transformant in the same manner as in the ordinary production through fermentation. Besides, GMT having a high purity can be obtained because the yield of GMT is higher and the amounts of impurities derived from the internal organs of animals are smaller than by the ordinary extraction method.

The GMT of the present invention is of high purity and of high activity, and can also be produced on an industrial scale. Accordingly, it is extremely useful as a reagent for measuring various enzymatic activities and as a reagent for clinical diagnosis.

What we claim is:

1. A recombinant vector containing a mutated recombinant rat glycine N-methyl transferase (GMT) gene on a plasmid, said recombinant vector is prepared by digesting with HindIII the DNA obtained from PCR amplification with a DNA containing rat GMT cDNA as template and PCR primers having the sequence of SEQ ID NO:3 and SEQ ID NO:4, and followed by inserting the HindIII-digested DNA into the plasmid digested with HindIII.

2. The recombinant vector according to claim 1, wherein the template DNA containing rat GMT cDNA comprises the sequence of SEQ ID NO:1.

3. The recombinant vector according to claim 2, wherein the plasmid is digested with NdeI and then filled in with Klenow before being digested with HindIII.

4. The recombinant vector according to claim 1 wherein the plasmid is pCW.

5. *Escherichia coli* host cell transformed with the recombinant vector of claim 1.

6. *Escherichia coli* host cell according to claim 5, which is *Escherichia coli* JM109/pCW-GMT, deposited as FERM BP-5078 at the National Institute of Bioscience and Human Technology, Japan.

7. A process for producing rat GMT, comprising the steps of:

culturing the *Escherichia coli* host of claim 6 to produce GMT; and recovering the GMT produced.

8. A recombinant vector containing a mutated recombinant rat glycine N-methyl transferase (GMT) gene on a plasmid, said recombinant vector is prepared by digesting with HindIII the DNA obtained from PCR amplification with a DNA containing rat GMT cDNA as template and PCR primers having the sequence of SEQ ID NO:3, where nucleotide position 20 is T, and SEQ ID NO:4, and followed by inserting the HindIII digested DNA into the plasmid digested with HindIII.

9. The recombinant vector according to claim 8, wherein the template DNA containing rat GMT cDNA comprises the sequence of SEQ ID NO:1.

10. The recombinant vector according to claim 9, wherein the plasmid is digested with NdeI and then filled in with Klenow before being digested with HindIII.

11. The recombinant vector according to claim 8 wherein the plasmid is pCW.

12. A recombinant vector containing a mutated recombinant rat glycine N-methyl transferase (GMT) gene on a plasmid, said recombinant vector is prepared by digesting with HindIII the DNA obtained from PCR amplification with a DNA containing rat GMT cDNA as template and PCR primers having the sequence of SEQ ID NO:3, where nucleotide position 20 is G, and SEQ ID NO:4, and followed by inserting the HindIII digested DNA into the plasmid digested with HindIII.

13. The recombinant vector according to claim 12, wherein the template DNA containing rat GMT cDNA comprises the sequence of SEQ ID NO:1.

14. The recombinant vector according to claim 13, wherein the plasmid is digested with NdeI and then filled in with Klenow before being digested with HindIII.

15. The recombinant vector according to claim 12 wherein the plasmid is pCW.

16. A recombinant vector comprising a mutated rat glycine N-methyl transferase (GMT) gene having the nucleotide sequence of SEQ ID NO:5.

17. A host cell transformed with the recombinant vector according to claim 16.

18. The transformed host cell according to claim 17, wherein the host cell is *Escherichia coli*.

19. The transformed host cell according to claim 17, which is *Escherichia coli* JM109/pCW-GMT, deposited as FERM BP-5078 at the National Institute of Bioscience and Human Technology, Japan.

20. A process for producing rat GMT, comprising the steps of:

culturing the transformed host cell of claim 17; and recovering the GMT produced.

* * * * *